United States Patent
Hsieh

(10) Patent No.: US 6,381,297 B1
(45) Date of Patent: Apr. 30, 2002

(54) HIGH PITCH RECONSTRUCTION OF MULTISLICE CT SCANS

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/639,368

(22) Filed: Aug. 15, 2000

(51) Int. Cl.$^7$ ................................................ A61B 6/03
(52) U.S. Cl. ........................................ 378/15; 378/901
(58) Field of Search .............................. 378/4, 15, 901

(56) References Cited

U.S. PATENT DOCUMENTS

| | | |
|---|---|---|
| 4,580,219 A | 4/1986 | Pelc et al. |
| 4,630,202 A | 12/1986 | Mori |
| 4,852,132 A | 7/1989 | Namikawa |
| 5,233,518 A | 8/1993 | King et al. |
| 5,848,117 A | 12/1998 | Urchuk et al. |
| 6,272,200 B1 * | 8/2001 | Pan et al. ..................... 378/15 |

OTHER PUBLICATIONS

Jiang Hsieh, "Reconstruction of X–Ray Helical Computed Tomography", *Medical Physics,* vol. 23, No. 2, Feb. 1996, pp. 221–229.

* cited by examiner

*Primary Examiner*—David V. Bruce
(74) *Attorney, Agent, or Firm*—Carl B. Horton, Esq.; Armstrong Teasdale LLP

(57) ABSTRACT

One embodiment of the present invention is a method for generating an image of an object using a multislice computed tomography imaging system. The method includes steps of: helically scanning an object with a multislice computed tomography imaging system to acquire projection data; determining a set of conjugate samples of the projection data that formulate a set of parallel projections; and reconstructing a set of images of the object using the conjugate samples. By determining a set of conjugate samples that formulate a set of parallel projections, embodiments of the present invention make possible reconstruction of images from projection data scanned at 8:1 pitch or higher.

22 Claims, 4 Drawing Sheets

HIGH PITCH RECONSTRUCTION OF MULTISLICE CT SCANS

BACKGROUND OF THE INVENTION

This invention relates generally to computed tomography (CT) imaging and more particularly to methods and apparatus for generating CT imaging data using a multi-slice imaging system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

The x-ray beam is projected from the x-ray source through a pre-patient collimator that defines the x-ray beam profile in the patient axis, or z-axis. The collimator typically includes x-ray-absorbing material with an aperture therein for restricting the x-ray beam. In at least one known CT imaging system, a scanning mode and corresponding reconstruction method are implemented for 3:1 and 6:1 helical pitches. The 6:1 helical pitch mode is referred to as a "high speed" mode because volume coverage is large, and scanning is faster along z-axis than in the 3:1 helical pitch mode. However, the scanning and reconstruction techniques used for this high speed mode have not been found suitable for scanning at greater helical pitches, for example, 8:1 or higher. One of several reasons that these techniques have not been found suitable is that the 6:1 high speed mode uses conjugate sampling pairs that are, in general, no longer valid at pitches of 8:1 or more.

For explaining the problems of the known high speed mode, it will be helpful to define a number of variables and their relationship to the geometry of a CT imaging system. Let $\beta_k$, k=1, . . . , 4 represent projection angles at which detector rows k intersect a plane of reconstruction. Also, let $\beta_{k-}$, k=1, . . . , 4 represent projection angles of conjugate samples for $\beta_k$ that are π earlier, so that $\beta_{k-}=\beta_k-\pi-2\gamma$. Similarly, let $\beta_{k+}$ represent projection angles of conjugate samples for $\beta_k$ that are π later so that $\beta_{k+}=\beta_k+\pi-2\gamma$.

In fan beam geometry, the detector angle, γ, is defined as an angle formed by any ray with respect to an isoray 50, as illustrated in FIG. 4. More particularly, $\gamma_m=\max(|\gamma|)$ represents a maximum fan angle. Referring to FIGS. 5 and 6, the four adjacent graphs 52, 54, 56, 58 represent the four adjacent detector rows of one known CT imaging system. Graph 52 represents the weighting region for detector row 1. Graphs 54, 56, and 58 are for detector rows 2, 3, and 4, respectively. The labeled regions in the graphs (R1, R2, . . . , R4) are regions in which weighting functions are applied to the projection samples. Outside these regions, all weights are equal to zero. Therefore, projection data outside these regions is not needed.

In each graph 52, 54, 56, 58, horizontal axis 60 represents the detector angle, γ, and vertical axis 62 represents the projection angle, β. Therefore, samples corresponding to a fan beam at a particular view angle are represented by horizontal lines in the graphs. Referring to FIG. 5, a lower boundary for region R1 (corresponding to detector row 1) represents conjugate samples of $\beta_3$. Therefore, the boundary is defined by $\beta_{3-}$.

As shown in FIG. 5, in high speed acquisition at 6:1, an iso-ray of $\beta_{3-}$ intersects detector row 1 when row 1 is one detector-row-width away from $\beta_1$, where $\beta_1$ is a projection angle at which row 1 crosses a plane of reconstruction. For a 6:1 helical pitch, a table of the CT imaging system travels six times a thickness of a detector in a gantry rotation of 2π. Therefore, it takes 2π/6=π/3 to travel a single detector thickness. (In FIG. 5, π/3 thickness is 1 division of the vertical axis.) The angular span for R2, R3 and R4 is π/3, and corresponds to a detector thickness. The lower right region defined by $\beta_{3-}$ of R1 (detector row 1) is nearly 2π/3 away from $\beta_1$, or almost twice a detector thickness away from a point at which detector row 1 intersects the plane of reconstruction. Thus, samples acquired far away from a true sample location are used to estimate an ideal sample, which adversely affects the accuracy of the estimation. This same problem also applies for regions R2' (for detector rows 2 and 4) and R1 for detector row 3. FIG. 6 represents a corresponding high-speed mode weighting pattern for 8:1 helical reconstruction, showing that the problem becomes even worse at this higher pitch.

Furthermore, the known 6:1 high speed mode reconstruction relies upon the existence of certain conjugate samples. In particular, and referring to FIG. 5 samples from rows 2 and 4 are used to perform interpolations in high speed mode, as are samples from rows 3 and 1. However, this mode is not suitable for scanning at helical pitches of 8:1 or higher. Referring to FIG. 6, it is clear that at these higher pitches, $\beta_{4-}$ and $\beta_1$ lines for row 1 intersect. Similarly, lines for $\beta_{1+}$ and $\beta_4$ for row 4 intersect. Because lines $\beta_{4-}$ and $\beta_{1+}$ should carry a weight of zero and $\beta_1$ and $\beta_4$, should carry a weight of 1, the weights for the intersecting points cannot be determined.

Another reason that the known high speed mode has not been found suitable for 8:1 and higher pitches is that an imaging system employing a 6:1 helical pitch is configured so that $\beta_1$, $\beta_2$, $\beta_3$, and $\beta_4$ are spaced $\pi/3$ apart, while $2\gamma_m$ is slightly less than $\pi/3$. When an 8:1 helical pitch is employed, $\beta_1$, $\beta_2$, $\beta_3$, and $\beta_4$ are spaced $\pi/4$ apart. This latter configuration no longer confines conjugate regions to one side of a location at which the detector crosses the POR, as shown by regions R1 in FIG. 6. A discontinuity is created in the weighting function at the boundaries of the two regions.

It is thus seen that the known high speed imaging mode is not suitable for imaging of objects at 8:1 pitch and higher. It would therefore be desirable to provide methods and apparatus that can overcome this limitation.

BRIEF SUMMARY OF THE INVENTION

There is therefore provided, in one embodiment of the present invention, a method for generating an image of an object using a multislice computed tomography imaging system. The method includes steps of: helically scanning an object with a multislice computed tomography imaging system to acquire projection data; determining a set of conjugate samples of the projection data that formulate a set of parallel projections; and reconstructing a set of images of the object using the conjugate samples.

By determining a set of conjugate samples that formulate a set of parallel projections, embodiments of the present invention make possible reconstruction of images from projection data scanned at pitches greater than 6:1, for example, 8:1 or higher.

DETAILED DESCRIPTION OF THE INVENTION

Figure 1:
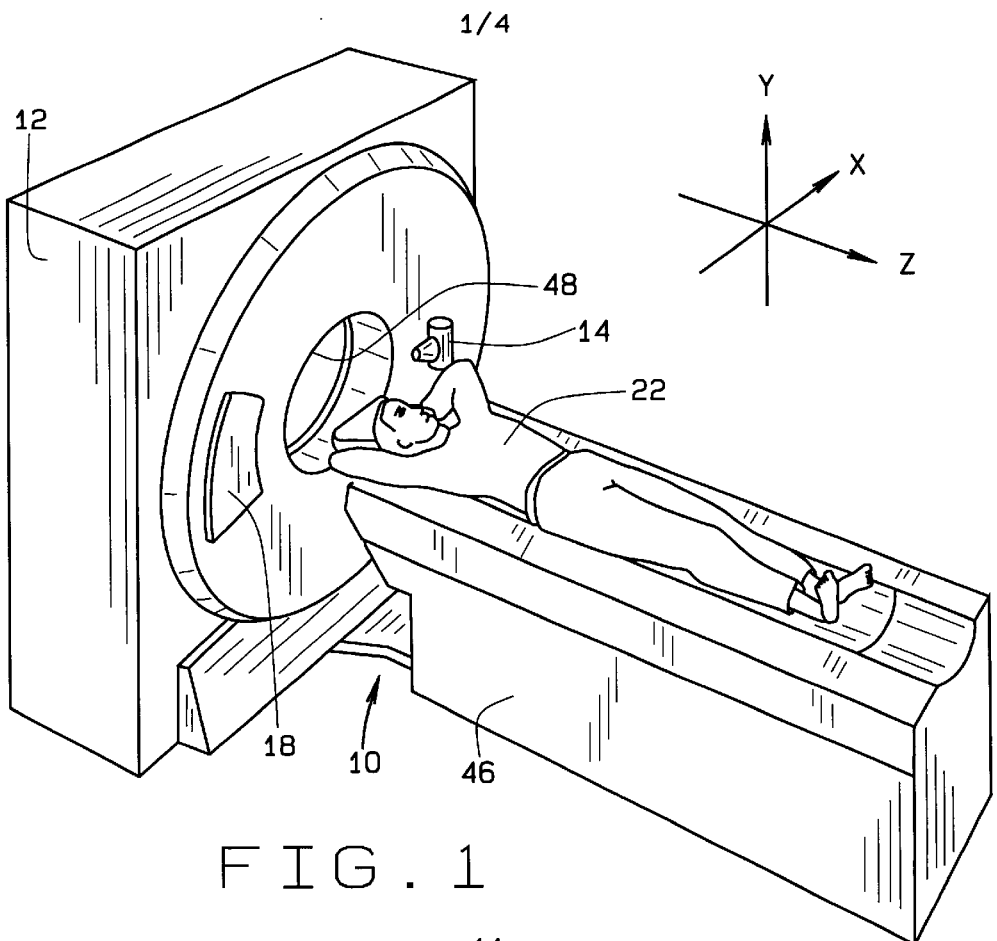
FIG. 1 is a pictorial view of a CT imaging system.
Figure 2:
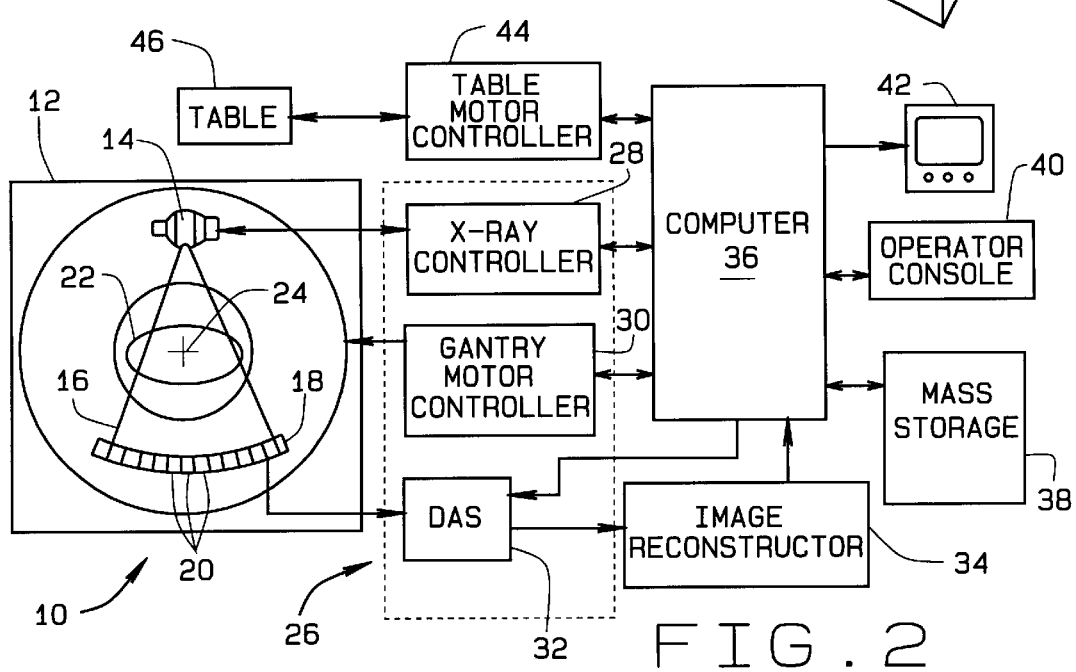
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam. As the x-ray beam passes through a patient 22, the bean is attenuated. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
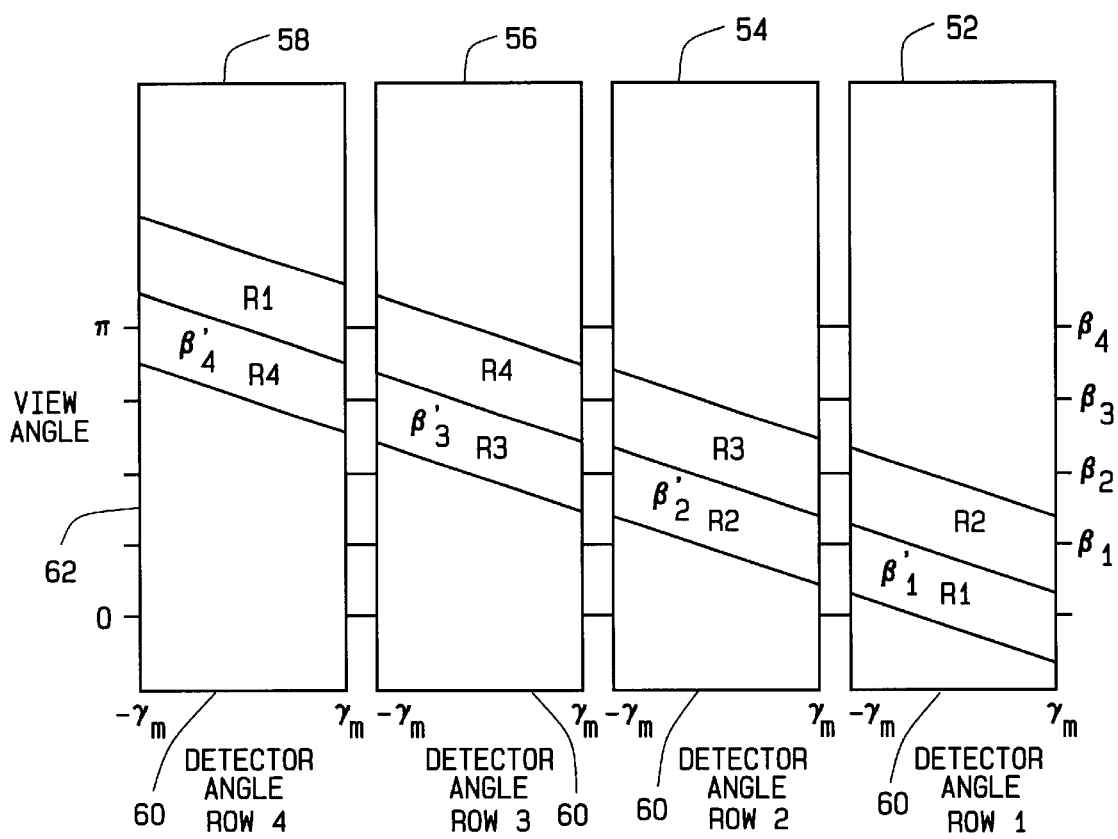
FIG. 3 is a drawing of four adjacent graphs representing four detector rows of a CT imaging system, the graphs representing weighting regions of the detector rows in one embodiment of the present invention at 8:1 helical pitch.
Figure 4:
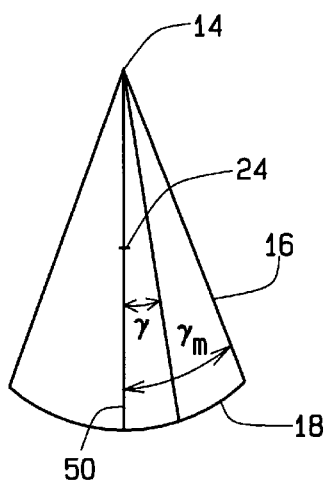
FIG. 4 is a diagram illustrating a fan beam geometry in which a detector angle, $\gamma$, is defined as an angle formed by any ray with respect to an isoray.
Figure 5:
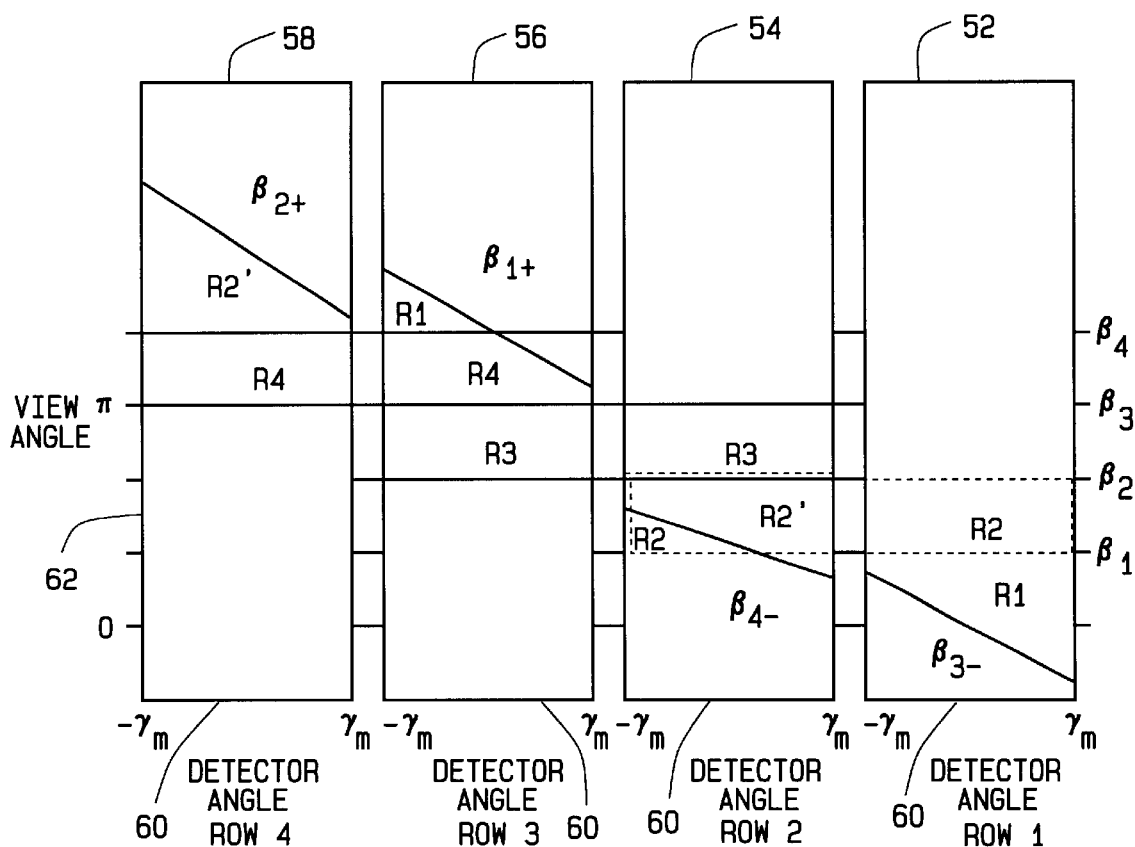
FIG. 5 is a drawing of four adjacent graphs representing four adjacent detector rows of a known CT imaging system, wherein each graph represents a weighting region for a detector row at 6:1 helical pitch.
Figure 6:
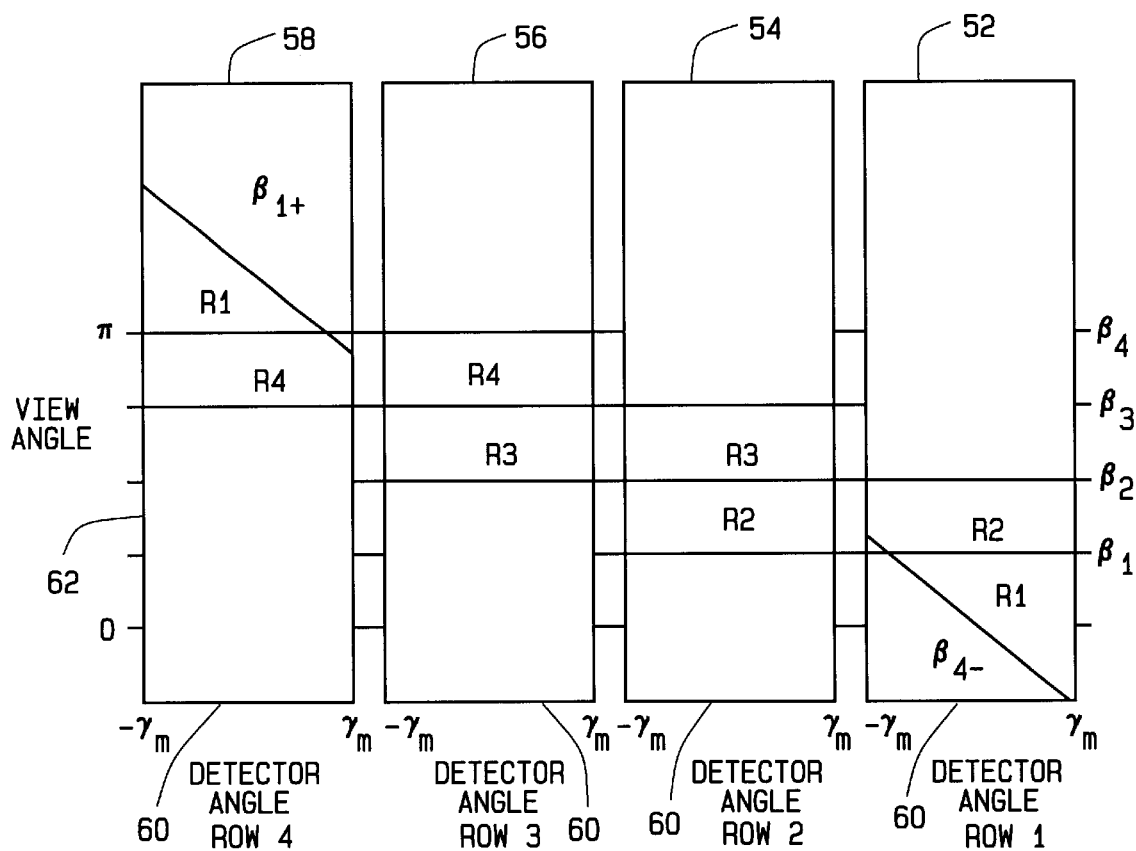
FIG. 6 is a drawing similar to that of FIG. 5, but representing corresponding weighting regions at 8:1 helical pitch.

One embodiment of the present invention searches for conjugate samples that formulate a set of parallel projections. More specifically, this embodiment sets region boundaries that are formulated by $\beta'_k$, k=1,2,3,4, where $\beta'_k=\beta_k-\gamma$. In this expression, $\beta_k$ is as defined above and also as labeled in FIGS. 4, 5, and 6. The $\beta'_k$ are as labeled in FIG. 3 as boundaries between two regions for each row. Thus, $\beta'_1$ is a boundary between regions R1 and R2 for detector row 1, and $\beta_i$ is a projection angle at which the iso-ray of detector-row i crosses POR. The corresponding parallel ray samples, $\beta'_i$, are written as:

$$\beta'_i = \beta_i - \gamma \tag{1}$$

In equation (1), $\gamma$ is the detector angle. Let us further define the quantities $\beta'_{i+} = \beta'_i + \pi$ and $\beta'_{i-} = \beta'_i - \pi$. Region pairs R1, R2, R3, and R4 that are interpolated to produce projections at POR are labeled as such in the representation shown in FIG. 3. Let us further denote by $w_i(\beta,\gamma)$ a projection weighting function applied to the detector-row i. The weighting function used for reconstruction in one embodiment of the present invention is written as:

$$w_1(\beta,\gamma) = \begin{cases} \dfrac{\beta - \beta'_{4-}}{\beta'_1 - \beta'_{4-}} & \beta'_{4-} \le \beta < \beta'_1 \\ \dfrac{\beta - \beta'_2}{\beta'_1 - \beta'_2} & \beta'_1 \le \beta < \beta'_2 \\ 0 & \text{otherwise} \end{cases} \tag{2}$$

$$w_2(\beta,\gamma) = \begin{cases} \dfrac{\beta - \beta'_1}{\beta'_2 - \beta'_1} & \beta'_1 \le \beta < \beta'_2 \\ \dfrac{\beta - \beta'_3}{\beta'_2 - \beta'_3} & \beta'_2 \le \beta < \beta'_3 \\ 0 & \text{otherwise} \end{cases} \tag{3}$$

-continued $$w_3(\beta, \gamma) = \begin{cases} \dfrac{\beta - \beta'_2}{\beta'_3 - \beta'_2} & \beta'_2 \le \beta < \beta'_3 \\ \dfrac{\beta - \beta'_4}{\beta'_3 - \beta'_4} & \beta'_3 \le \beta < \beta'_4 \\ 0 & \text{otherwise} \end{cases} \quad (4)$$

$$w_4(\beta, \gamma) = \begin{cases} \dfrac{\beta - \beta'_3}{\beta'_4 - \beta'_3} & \beta'_3 \le \beta < \beta'_4 \\ \dfrac{\beta - \beta'_{1+}}{\beta'_4 - \beta'_{1+}} & \beta'_4 \le \beta < \beta'_{1+} \\ 0 & \text{otherwise} \end{cases} \quad (5)$$

In an experiment to show the effectiveness of the weighting function $w_i(\beta, \gamma)$, a shoulder phantom was scanned in 4×1.25 mm mode at 6:1 helical pitch and 8:1 helical pitch. For the 6:1 helical pitch, a conventional "high speed" reconstruction mode was used (i.e., the reconstruction method searched for and used conjugate samples that correspond to samples of a single projection). The 8:1 helical pitch scan was reconstructed using an embodiment of the present invention, using equations (2)–(5) above. All other things being equal, higher helical pitches would be expected to produce more pronounced image artifacts as a result of projection inconsistency. However, it was found that the artifact level for the 8:1 pitch images was only slightly higher than for the 6:1 pitch images. This result indicates the effectiveness of the embodiment of the present invention in combating image artifacts. In another experiment, the 6:1 pitch scans were reconstructed using the same embodiment used to reconstruct the 8:1 pitch scans. It was found that the images obtained from the 6:1 pitch scans were quite comparable in terms of image artifacts to those of the 8:1 pitch scans. This is another indication of the effectiveness of this embodiment of the present invention in combating image artifacts due to helical scans.

It will thus be recognized that embodiments of the present invention overcome the limitations of at least one high-speed CT image reconstruction method and apparatus and provide improved images at helical pitches greater than 6:1. While the invention has been described in terms of various specific embodiments, those skilled in the art will recognize that the invention can be practiced with modification within the spirit and scope of the claims.

What is claimed is:

1. A method for generating an image of an object using a multislice computed tomography imaging system, said method comprising the steps of:
   helically scanning an object with a multislice computed tomography imaging system to acquire projection data;
   determining a set of conjugate samples of the projection data that formulate a set of parallel projections; and
   reconstructing a set of images of the object using the conjugate samples.

2. A method in accordance with claim 1 wherein reconstructing a set of images of the object using the conjugate samples comprises the steps of weighting the parallel projections based on the conjugate samples, and reconstructing a set of images using the weighted parallel projections.

3. A method in accordance with claim 1 wherein the multislice computed tomography imaging system comprises a detector having a plurality of parallel rows of detector elements configured to acquire projection data, and an x-ray source configured to project an x-ray beam, including an iso-ray, towards the detector through an object being scanned;
and wherein determining a set of conjugate samples of the projection data that formulate a set of parallel projections comprises the step of setting region boundaries formulated by $\beta_k$–$\gamma$, where $\beta_k$ is a projection angle at which detector row k intersects a plane of reconstruction.

4. A method in accordance with claim 3 wherein reconstructing a set of images of the object from the set of parallel projections comprises the step of interpolating pairs of regions defined by the region boundaries to produce projections at a plane of reconstruction (POR).

5. A method in accordance with claim 4 wherein reconstructing a set of images of the object from the set of parallel projections comprises the step of applying a weighting function determined as a continuous function of a projection angle $\beta$ to the projections at a plane of reconstruction for each image slice to be reconstructed.

6. A method in accordance with claim 5 wherein helically scanning an object with a multislice computed tomography imaging system to acquire projection data comprises the step of scanning the object at a helical pitch greater than 6:1.

7. A method in accordance with claim 6 wherein helically scanning an object with a multislice computed tomography imaging system to acquire projection data comprises the step of scanning the object at a helical pitch of 8:1.

8. A method in accordance with claim 7 wherein helically scanning an object with a multislice computed tomography imaging system to acquire projection data comprises the step of operating the computed tomography imaging system to acquire projection data representing four image slices, and wherein reconstructing a set of images of the object from the set of parallel projections comprises the step of reconstructing four images.

9. A method in accordance with claim 4 wherein helically scanning an object with a multislice computed tomography imaging system to acquire projection data comprises the step of operating the computed tomography imaging system to acquire projection data representing four image slices;

wherein applying a weighting function determined as a continuous function of a projection angle $\beta$ to the projections at a plane of reconstruction for each image slice to be reconstructed comprises the step of applying weighting functions written as:

$$w_1(\beta, \gamma) = \begin{cases} \dfrac{\beta - \beta'_{4-}}{\beta'_1 - \beta'_{4-}} & \beta'_{4-} \le \beta < \beta'_1 \\ \dfrac{\beta - \beta'_2}{\beta'_1 - \beta'_2} & \beta'_1 \le \beta < \beta'_2 \\ 0 & \text{otherwise} \end{cases}$$

$$w_2(\beta, \gamma) = \begin{cases} \dfrac{\beta - \beta'_1}{\beta'_2 - \beta'_1} & \beta'_1 \le \beta < \beta'_2 \\ \dfrac{\beta - \beta'_3}{\beta'_2 - \beta'_3} & \beta'_2 \le \beta < \beta'_3 \\ 0 & \text{otherwise} \end{cases}$$

$$w_3(\beta, \gamma) = \begin{cases} \dfrac{\beta - \beta'_2}{\beta'_3 - \beta'_2} & \beta'_2 \le \beta < \beta'_3 \\ \dfrac{\beta - \beta'_4}{\beta'_3 - \beta'_4} & \beta'_3 \le \beta < \beta'_4 \\ 0 & \text{otherwise} \end{cases}$$

-continued $$w_4(\beta, \gamma) = \begin{cases} \dfrac{\beta - \beta'_3}{\beta'_4 - \beta'_3} & \beta'_3 \leq \beta < \beta'_4 \\ \dfrac{\beta - \beta'_{1+}}{\beta'_4 - \beta'_{1+}} & \beta'_4 \leq \beta < \beta'_{1+} \\ 0 & \text{otherwise} \end{cases}$$

where:

$w_i$ ($\beta,\gamma$) is a projection weighting function applied to a detector row i;

$\gamma$ is a detector angle;

$\beta_i$ is a projection angle at which an iso-ray of detector row i crosses a plane of reconstruction;

$\beta'_i = \beta_i - \gamma$ is an angle of a parallel ray sample corresponding to a projection angle $\beta_i$ of that sample; and $\beta'_{i+} = \beta'_i + \pi$ and $\beta'_{i-} = \beta'_i - \pi$.

10. A method in accordance with claim 9 wherein helically scanning an object with a multislice computed tomography imaging system to acquire projection data comprises the step of scanning the object at a helical pitch greater than 6:1.

11. A method in accordance with claim 10 wherein helically scanning an object with a multislice computed tomography imaging system to acquire projection data comprises the step of scanning the object at a helical pitch of 8:1.

12. A multislice computed tomography system configured to:

helically scan an object to acquire projection data;

determine a set of conjugate samples of the projection data that formulate a set of parallel projections; and reconstruct a set of images of the object using the conjugate samples.

13. A system in accordance with claim 12 wherein to reconstruct a set of images of the object using the conjugate samples, said system is configured to weight the parallel projections based on the conjugate samples, and to reconstruct a set of images using the weighted parallel projections.

14. A system in accordance with claim 12 wherein said system comprises a detector having a plurality of parallel rows of detector elements configured to acquire projection data, and an x-ray source configured to project an x-ray beam, including an iso-ray, towards the detector through an object being scanned;

and wherein to determine a set of conjugate samples of the projection data that formulate a set of parallel projections, said system is configured to determine a set of region boundaries formulated by $\beta_k - \gamma$, where $\beta_k$ is a projection angle at which detector row k intersects a plane of reconstruction.

15. A system in accordance with claim 14 wherein to reconstruct a set of images of the object from the set of parallel projections, said system is configured to interpolate pairs of regions defined by the region boundaries to produce projections at a plane of reconstruction (POR).

16. A system in accordance with claim 15 wherein to reconstruct a set of images of the object from the set of parallel projections, said system is configured to apply a weighting function determined as a continuous function of a projection angle $\beta$ to the projections at a plane of reconstruction for each image slice to be reconstructed.

17. A system in accordance with claim 16 wherein said system is configured to helically scan the object at a helical pitch greater than 6:1.

18. A system in accordance with claim 17 wherein said system is configured to helically scan an object at a helical pitch of 8:1.

19. A system in accordance with claim 18 wherein said system being configured to helically scan an object to acquire projection data comprises said system being configured to acquire projection data representing four image slices, and wherein said system being configured to reconstruct a set of images of the object from the set of parallel projections comprises said system being configured to reconstruct four images.

20. A system in accordance with claim 15 wherein said system being configured to helically scan an object comprises said system being configured to acquire projection data representing four image slices; and wherein said system being configured to apply a weighting function determined as a continuous function of a projection angle $\beta$ to the projections at a plane of reconstruction for each image slice to be reconstructed comprises said system being configured to apply weighting functions written as:

$$w_1(\beta, \gamma) = \begin{cases} \dfrac{\beta - \beta'_{4-}}{\beta'_1 - \beta'_{4-}} & \beta'_{4-} \leq \beta < \beta'_1 \\ \dfrac{\beta - \beta'_2}{\beta'_1 - \beta'_2} & \beta'_1 \leq \beta < \beta'_2 \\ 0 & \text{otherwise} \end{cases}$$

$$w_2(\beta, \gamma) = \begin{cases} \dfrac{\beta - \beta'_1}{\beta'_2 - \beta'_1} & \beta'_1 \leq \beta < \beta'_2 \\ \dfrac{\beta - \beta'_3}{\beta'_2 - \beta'_3} & \beta'_2 \leq \beta < \beta'_3 \\ 0 & \text{otherwise} \end{cases}$$

$$w_3(\beta, \gamma) = \begin{cases} \dfrac{\beta - \beta'_2}{\beta'_3 - \beta'_2} & \beta'_2 \leq \beta < \beta'_3 \\ \dfrac{\beta - \beta'_4}{\beta'_3 - \beta'_4} & \beta'_3 \leq \beta < \beta'_4 \\ 0 & \text{otherwise} \end{cases}$$

$$w_4(\beta, \gamma) = \begin{cases} \dfrac{\beta - \beta'_3}{\beta'_4 - \beta'_3} & \beta'_3 \leq \beta < \beta'_4 \\ \dfrac{\beta - \beta'_{1+}}{\beta'_4 - \beta'_{1+}} & \beta'_4 \leq \beta < \beta'_{1+} \\ 0 & \text{otherwise} \end{cases}$$

where:

$w_i$ ($\beta,\gamma$) is a projection weighting function applied to a detector row i;

$\gamma$ is a detector angle;

$\beta_i$ is a projection angle at which an iso-ray of detector row i crosses a plane of reconstruction;

$\beta'_i = \beta_i - \gamma$ is an angle of a parallel ray sample corresponding to a projection angle $\beta_i$ of that sample; and $\beta'_{i+} = \beta'_i + \pi$ and $\beta'_{i-} = \beta'_i - \pi$.

21. A system in accordance with claim 20 wherein said system is configured to scan the object at a helical pitch greater than 6:1.

22. A system in accordance with claim 21 wherein said system is configured to scan the object at a helical pitch of 8:1.

* * * * *